United States Patent [19]

Takino et al.

[11] Patent Number: 4,631,255
[45] Date of Patent: Dec. 23, 1986

[54] COMPOSITION FOR ASSAYING FOR NITRITES

[75] Inventors: Kiyoko Takino, Akishima; Hidetoshi Asahi, Kokubunji; Hiroshi Wada, Chigasaki, all of Japan

[73] Assignee: Eiken Kagaku Kabushiki Kaisha, Japan

[21] Appl. No.: 682,143

[22] Filed: Dec. 17, 1984

[30] Foreign Application Priority Data

Jul. 23, 1984 [JP] Japan .................. 59-152509

[51] Int. Cl.$^4$ .................. C12Q 1/12; G01N 33/00
[52] U.S. Cl. .................. 435/37; 436/110
[58] Field of Search .................. 435/37; 436/110

[56] References Cited

U.S. PATENT DOCUMENTS

| | | | |
|---|---|---|---|
| 3,415,717 | 12/1968 | Avakian | 435/37 |
| 3,634,198 | 1/1972 | Truhan | 435/37 |
| 3,645,853 | 2/1972 | Kronish et al. | 435/37 X |
| 3,712,853 | 1/1973 | Rittersdorf et al. | 435/37 |
| 3,785,929 | 1/1974 | Kronish et al. | 435/37 |
| 3,817,705 | 6/1974 | Stein et al. | 436/110 |

FOREIGN PATENT DOCUMENTS 55-10027  3/1980  Japan.

OTHER PUBLICATIONS

Fischl et al., "Rapid Spot Tests for Routine Urine Analysis", Clinica Chimica Acta, vol. 2, pp. 527–533 (1957).
Raymond Schaus, "Griess' Nitrite Test in Diagnosis of Urinary Infection", J.A.M.A., Jun. 9, 1956, pp. 528–529.
Oda et al., "Kogyo Kagaku Zassi" 59, No. 9, pp. 1028–1030 (1956).
Greiss, "Bemerkungen zu der Abhandlung der HH. Weselsky and Benedikt Ueber einige Azoverbindungen", Chemishe Berichte, 12, 426–7 (1879).
Schaus, R., JAMA, 161(6), 528 (1956).
Schersten, B., Dahlqvist, A., Fritz, H., Kohler, L. & Westlumd, L., JAMA, 204, 205 (1968).
"New Method for Catalase Determination", Gagnon et al., Analytical Chemistry, 31, 144–148, 1959.
"A Test for Bacteriuria", Williams & Simmons, Lancet, 1, pp. 1373–1374, 1963.

Primary Examiner—Robert J. Warden
Assistant Examiner—Patricia Kate White
Attorney, Agent, or Firm—Parkhurst & Oliff

[57] ABSTRACT

A composition for assaying nitrites comprising a diazotizable amine, an acid component and a coupling component, wherein the coupling component is a compound of the following formula I:

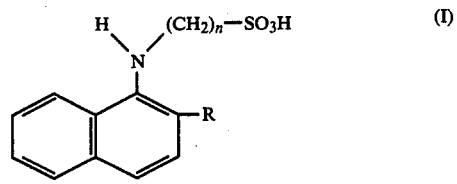

wherein R represents a hydrogen atom or a straight-chain alkyl group having 1 to 6 carbon atoms, such as a methyl, ethyl, n-propyl, n-butyl, n-pentyl or n-hexyl group and n represents an integer of 1 to 6, with the proviso that the sulfoalkyl group may be substituted with at least 1 hydroxyl group, or a water-soluble salt thereof as well as test devices carrying the composition. This composition is far more sensitive than conventional compositions for assaying nitrites. With this composition, for example, a trace amount of as small as 0.02 mg/100 ml of a nitrite to be detected in urine in the diagnosis of a bacterial infection such as urinary tract infection can be detected surely.

14 Claims, 1 Drawing Figure

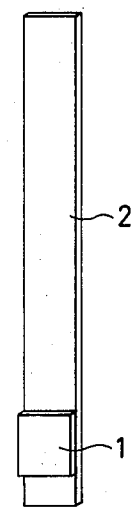

COMPOSITION FOR ASSAYING FOR NITRITES

BACKGROUND OF THE INVENTION

1. Field of the Invention

The present invention relates to a composition for detecting nitrites or nitrite-forming bacteria in foods and body fluids, particularly urine.

2. Description of the Prior Art

The frequency of occurrence of urinary tract infection is high. This disease is asymptomatic and the patients are women in most cases. When bacteriuria patients are left untreated, they suffer from manifest urinary tract infection frequently to cause various problems. However, an early diagnosis of the infection is possible by detecting bacteria excreted in the urine. When the diagnosis is to be effected biologically, urine is taken in such a manner that it is not contaminated with persistent bacteria. After a quantitative culture, at least $10^5$/ml of the bacteria should be detected. However, the quantitative culture requires a complicated technique and a long time. Therefore, a chemical method has been employed for the rough quantitative determination of the bacteria more easily and rapidly.

Bacteria such as *E. coli* (the most common bacterium causing urinary tract infection), Proteus, Klebsiella, Staphylococcus and Enterococcus contain in their microbial bodies an enzyme which reduces nitrates into nitrites. Vesical urine of a healthy person is free from bacteria and, therefore, when a nitrite is detected in urine, it may be considered that a urinary tract such as renal pelvis or bladder is infected with one or more of the above-mentioned bacteria and that a nitrate in urine was reduced into a corresponding nitrite in the infected part.

A known, highly sensitive method of detecting bacteria in the urinary tract is based on the determination of the nitrite in excreted urine by a Griess test. A typical reagent for determining the nitrite by this test comprises an acidic solution of sulfanilic acid and 1-naphthylamine. In the Griess test, a nitrite contained in a sample diazotizes sulfanilic acid and a resulting diazonium salt is coupled with 1-naphthylamine to form a red dye. The concentration of this dye is proportional to the concentration of the nitrite. Therefore, the concentration of the nitrite can be determined by, for example, colorimetric analysis using a previously prepared calibration curve. This method had demerits in that the reagent solution is unstable and the operation is troublesome. To overcome these demerits, a method has been proposed wherein the Griess test is conducted on a carrier on which the reagent composition has been fixed.

In the field of so-called "dry chemistry" in which a reagent composition used for the assay of a body fluid composition is fixed on a carrier, a reagent composition comprising sulfanilic acid, 1-naphthylamine and a solid organic acid has been known (see Fischl & Pinto "Clin. Chim. Acta" 2, 527–533 (1957). Such a reagent mixture in dry state is far more stable than the solution so that it can be stored for a long time. Another example of the assaying agents is a reagent mixture comprising a diazotizable amine, an N,N-dialkyl-2-naphthylamine and a solid organic acid as disclosed in the specification of U.S. Pat. No. 3,415,717. However, these known test pieces have a minimum detection limit of 0.1 to 1 mg/100 ml in terms of sodium nitrite. Such a low sensitivity is insufficient for detecting only a trace of the nitrite to be detected in the examination of bacterial infection. Under these circumstances, the development of highly sensitive and stable test pieces has been demanded.

After intensive investigations made for the purpose of overcoming the above-mentioned defects of the conventional methods, the inventors have completed the present invention.

SUMMARY OF THE INVENTION

The present invention aims at solving the problems of the prior art. An object of the invention is to provide a stable composition for assaying nitrites which has a sensitivity sufficient for assaying nitrites to be detected in patients with bacterial infections, and also test devices carrying said composition.

The composition of the present invention for assaying for nitrites comprises a diazotizable amine, an acid component and a coupling component, wherein said coupling component is a compound of the following general formula I:

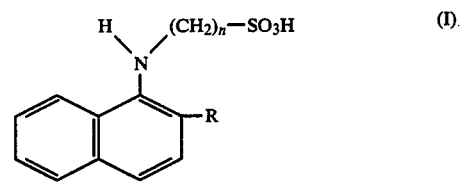

wherein R represents a hydrogen atom or a straight-chain alkyl group having 1 to 6 carbon atoms, such as a methyl, ethyl, n-propyl, n-butyl, n-pentyl or n-hexyl group and n represents an integer of 1 to 6 with the proviso that the sulfoalkyl group may be substituted with at least 1 hydroxyl group, or a water-soluble salt thereof.

BRIEF DESCRIPTION OF THE DRAWING

The FIGURE is a perspective view of an embodiment of a test device carrying the composition of the present invention for assaying for nitrites.

DETAILED DESCRIPTION OF THE INVENTION

The inventors have found that when the compound of the above general formula (I) or a water-soluble salt thereof is used as the coupling component, nitrites to be detected in the bacterial infections (in only a trace amount, i.e., 0.02 mg/100 ml of the nitrites) can be assayed quantitatively in a highly sensitive manner.

The compounds preferably used as the coupling component in the present invention include, for example, the following compounds, though they are not limited thereto:

N-(1-naphthyl)-3-aminopropanesulfonic acid,
N-(2-methyl-1-naphthyl)-3-aminopropanesulfonic acid,
N-(2-ethyl-1-naphthyl)-3-aminopropanesulfonic acid,
N-(1-naphthyl)-4-aminobutanesulfonic acid,
N-(1-naphthyl)-2-aminoethanesulfonic acid, and
N-(1-naphthyl)-3-amino-2-hydroxypropanesulfonic acid.

Though most of these compounds have not been disclosed in literature as yet, they can be prepared easily by known processes.

For example, these compounds can be obtained by reacting 1-naphthylamine with a corresponding sultone (see Oda et al. "Kogyo Kagaku Zasshi" 59, No. 9, 1028 to 1030 (1956)) or by reacting 1-naphthylamine with an alkylsulfonic acid or hydroxyalkylsulfonic acid having a halogen atom at its terminal (see N. E. Good et al., "Analytical Biochemistry", 104, 300 to 310 (1980)).

The composition of the present invention for assaying for nitrites is obtained by mixing the obtained coupling component with a diazotizable amine and an acid component. When the composition of the present invention is incorporated in an absorptive carrier and the carrier is applied to a support made of, for example, plastic so as to use it conveniently, a test device having an excellent storage stability and being usable easily is obtained. The most frequently used absorptive carrier is filter paper. In addition, non-woven fabrics, cotton and wood pieces may also be used. It is also possible to apply the assaying composition to a support such as a sheet of plastics, e.g., polyvinyl chloride, polystyrene, or polyester, together with a suitable adhesive such as gelatin or a synthetic resin, e.g. polyvinyl alcohol. After drying, the composition is fixed on the support. It will be understood that various modifications can be readily obtained.

The diazotizable amines include, for example, sulfanilic acid, arsanilic acid, p-aminobenzoic acid and particularly sulfanilamide.

The acid components include solid organic acids such as tartaric, citric, oxalic, malic, malonic, succinic and glutaric acids. Among them, tartaric, citric and oxalic acids are preferred.

The test devices may be prepared by, for example, the following process: the diazotizable amine, coupling component and solid organic acid are dissolved in water, an organic solvent, or a mixture of water and organic solvent to attain given concentrations. An absorptive carrier, preferably a filter paper, is immersed in the resulting solution and then the carrier is taken out and dried to obtain a test paper. The test paper is cut into pieces having a desired size and a desired shape and then applied to a support such as a plastic sheet to obtain the test pieces carrying the nitrite-assaying composition of the present invention.

The amount of the diazotizable amine is 0.5 to 10 mM, preferably 1 to 7 mM and more preferably 1.5 to 5 mM, per 100 ml of the solution. The amount of the coupling component is 0.1 to 5 mM, preferably 0.2 to 3 mM and more preferably 0.5 to 2 mM. The molar ratio of the diazotizable amine to the coupling component is in the range of 1/2 to 7/1, preferably 3/1 to 6/1 (practically, the reaction ratio is 1/1).

The concentration of the solid organic acid is 2 to 15 wt. %, preferably 2.5 to 12 wt. % and more preferably 3 to 8 wt. % based on the amount of the composition solution.

Suitable organic solvents for the above-mentioned components are lower aliphatic alcohols, particularly methanol. As a matter of course, other easily evaporable solvents in which the respective components are soluble may also be used.

The test devices are not only suitable for detecting nitrite-forming bacteria in urine but are also usable generally for detecting nitrities or nitrite-forming bacteria such as those in drinking water or foods.

DESCRIPTION OF THE PREFERRED EMBODIMENTS

The following examples will further illustrate the present invention, which by no means limit the invention.

Preparation of coupling components

Preparation Example 1

Synthesis of sodium N-(1-naphthyl)-3-aminopropanesulfonate:

11.8 g of 1-naphthylamine was dissolved in 300 ml of 1-propanol. A solution of 10.1 g of 1,3-propanesultone in 20 ml of methanol was added to the above solution and the mixture was heated under reflux for about 3 h. After cooling to room temperature, the mixture was neutralized with a 1N aqueous NaOH solution and then the solvent was evaporated to dryness. After recrystallization from a solvent mixture of methanol and benzene, 7.8 g of white crystals were obtained (yield: 33%).

Physical properties:

Thin layer chromatography (silica gel plate (a product of Merck Co.); developer: chloroform/methanol/water=8/5/2)

UV absorption observed ninhydrin reaction (+)

Rf=0.14

Infrared absorption spectrum (KBr tablet, $\nu_{max}$ (cm$^{-1}$)) $\nu_{SO_3}$ 1200, 1050 cm$^{-1}$; $\nu_{NH}$ 3400 cm$^{-1}$ $\nu_{C=C}$ 1620 cm$^{-1}$; $\nu_{CH_2}$ 2850 cm$^{-1}$ Melting point: 208° to 209° C. (decomposition)

Preparation Example 2

Synthesis of sodium N-(2-methyl-1-naphthyl)-3-aminopropanesulfonate:

12.6 g of 2-methyl-1-naphthylamine was dissolved in 300 ml of 1-propanol. A solution of 9.8 g of 1,3-propanesultone in 20 ml of methanol was added to the above solution and the mixture was heated under reflux for about 3 h. After cooling to room temperature, the mixture was neutralized with a 1N aqueous NaOH solution and then the solvent was evaporated to dryness. After recrystallization from a solvent mixture of methanol and benzene, 4.4 g of white crystals were obtained (yield: 18%).

Physical properties:

Thin layer chromatography (silica gel plate (a product of Merck Co.); developer: chloroform/methanol/water=8/5/2)

UV absorption observed ninhydrin reaction (+)

Rf=0.33

Infrared absorption spectrum (KBr tablet, $\nu_{max}$(cm$^{-1}$)) $\nu_{SO_3}$1200, 1050 cm$^{-1}$; $\nu_{NH}$ 3400 cm$^{-1}$ $\nu_{C=C}$ 1620 cm$^{-1}$; $\nu_{CH_2}$ 2930 cm$^{-1}$ $\nu_{CH_3}$ 2950 cm$^{-1}$ Melting point: 228° to 229° C. (decomposition)

Preparation of the composition for assaying for nitrites

EXAMPLE 1

0.3 g of sulfanilamide, 0.2 g of sodium N-(1-naphthyl)-3-aminopropanesulfonate and 3.0 g of tartaric acid were dissolved in a suitable amount of methanol. Additional methanol was added to the solution to prepare 100 ml of a solution of the composition of the present invention for assaying for nitrites in methanol.

EXAMPLES 2 to 9

Compositions of the present invention were prepared in the same manner as in Example 1 using various diazotizable amines, coupling components and acid components.

Comparative Example

A conventional composition for assaying for nitrites was prepared in the same manner as in Example 1 except that sodium N-(1-naphthyl)-3-aminopropanesulfonate was replaced with 1-naphthylamine.

The compositions for assaying nitrites prepared in the above examples and comparative example are summarized in Table 1.

Example 1 was replaced with a composition prepared in each of Examples 2 to 9.

Comparative Example 2

Test pieces were prepared in the same manner as in Example 10 except that the composition prepared in Example 1 was replaced with the composition prepared in Comparative Example 1.

TABLE 1

| No. | Composition for assaying for nitrites | | | |
|---|---|---|---|---|
| | Diazotizable amine | Coupling component | Acid component | Solvent |
| Ex. 1 | sulfanilamide (0.3 g, 1.7 mM) | sodium N—(1-naphthyl)-3-aminopropanesulfonate (0.2 g, 0.7 mM) | tartaric acid (3.0 g, 20 mM) | methanol (total 100 ml) |
| Ex. 2 | sulfanilic acid (2 mM) | sodium N—(1-naphthyl)-3-aminopropanesulfonate (0.2 g, 0.7 mM) | citric acid (5.0 g, 26 mM) | ethanol (total 100 ml) |
| Ex. 3 | arsanilic acid (2 mM) | sodium N—(1-naphthyl)-3-aminopropanesulfonate (0.2 g, 0.7 mM) | citric acid (5.0 g, 26 mM) | ethanol (total 100 ml) |
| Ex. 4 | p-aminobenzoic acid (2 mM) | sodium N—(1-naphthyl)-3-aminopropanesulfonate (0.2 g, 0.7 mM) | citric acid (5.0 g, 26 mM) | ethanol (total 100 ml) |
| Ex. 5 | p-aminobenzamide (2 mM) | sodium N—(1-naphthyl)-3-aminopropanesulfonate (0.2 g, 0.7 mM) | citric acid (5.0 g, 26 mM) | ethanol (total 100 ml) |
| Ex. 6 | sulfanilamide (0.3 g, 1.7 mM) | N—(2-methyl-1-naphthyl)-3-aminopropanesulfonic acid (2 mM) | citric acid (5.0 g, 26 mM) | ethanol (total 100 ml) |
| Ex. 7 | sulfanilamide (0.3 g, 1.7 mM) | N—(2-ethyl-1-naphthyl)-3-aminopropanesulfonic acid (2 mM) | citric acid (5.0 g, 26 mM) | ethanol (total 100 ml) |
| Ex. 8 | sulfanilamide (0.3 g, 1.7 mM) | N—(1-naphthyl)-4-aminobutanesulfonic acid (2 mM) | citric acid (5.0 g, 26 mM) | ethanol (total 100 ml) |
| Ex. 9 | sulfanilamide (0.3 g, 1.7 mM) | N—(1-naphthyl)-2-aminoethanesulfonic acid (2 mM) | citric acid (5.0 g, 26 mM) | ethanol (total 100 ml) |
| Comp. Ex. 1 | sulfanilamide (0.3 g, 1.7 mM) | 1-naphthylamine (0.1 g, 0.7 mM) | tartaric acid (3.0 g, 20 mM) | methanol (total 100 ml) |

Preparation of test pieces for assaying for nitrites

EXAMPLE 10

A filter paper (No. 2316; a product of Schleicher & Schüll Co.) was immersed in the composition prepared in Example 1 for a given time and then taken out and dried. The resulting test paper was cut into pieces of 5 mm × 5 mm and applied to an end of a polystyrene sheet of 5 mm × 80 mm by means of a double-coated adhesive tape (thickness: 0.35 mm) to obtain a test piece carrying the composition of the present invention for assaying nitrite concentration as shown in the FIGURE, wherein 1 indicates the test paper and 2 indicates a support, e.g., polystyrene sheet. The support may have numerals, letters, symbols, standard color tone, etc. applied to the surface thereof or printed thereon, if desired.

EXAMPLES 11 TO 18

Test pieces were prepared in the same manner as in Example 10 except that the composition prepared in

Performance comparison test

The test pieces for assaying nitrite concentration prepared in Examples 10 to 18 and Comparative Example 2 were immersed in urine containing a nitrite of various concentrations to estimate their analytical accuracy.

The results of the performance comparison tests of the test pieces for assaying nitrite concentration prepared in Examples 10 to 18 and Comparative Example 2 are summarized in Table 2.

TABLE 2

| No. | Results of the performance comparison tests | | |
|---|---|---|---|
| | Supported composition | Developed color tone[1] | Lower limit of detection (mg/100 ml) |
| Ex. 10 | Ex. 1 | light red to reddish purple | 0.02–0.03 |
| Ex. 11 | Ex. 2 | light reddish purple to purple | 0.02–0.03 |
| Ex. 12 | Ex. 3 | rose pink to red | 0.02–0.03 |
| Ex. 13 | Ex. 4 | light red to reddish purple | 0.02–0.03 |
| Ex. 14 | Ex. 5 | light red to reddish purple | 0.02–0.03 |
| Ex. 15 | Ex. 6 | rose pink to red | 0.02–0.04 |
| Ex. 16 | Ex. 7 | rose pink to red | 0.02–0.04 |
| Ex. 17 | Ex. 8 | light reddish purple to purple | 0.02–0.04 |
| Ex. 18 | Ex. 9 | light red to reddish purple | 0.02–0.04 |
| Comp. Ex. 2 | Comp. Ex. 1 | rose pink to red | 0.1–0.12 |

[1]The color tone was fixed after about 10 to 20 sec.

It is apparent from the results shown in Table 2 that the test pieces carrying the composition of the present invention for assaying for nitrites had a lower limit of detection of ⅓ to 1/5 of that of the conventional test pieces. This fact suggests that the detection sensitivity of the test pieces according to the present invention has been improved remarkably.

As described above in detail, the composition for assaying nitrites and test devices carrying the composition of the present invention are far more sensitive than the conventional composition for assaying nitrites and test devices carrying the composition. According to the present invention, a trace amount of as small as 0.02 mg/100 ml of a nitrite to be detected in urine in the diagnosis of a bacterial infection such as urinary tract infection can be detected surely.

Thus, the composition of the present invention and test pieces carrying the composition exhibit excellent effects in the highly sensitive detection of nitrites in various samples as well as in the easy and rapid assay thereof.

What is claimed is:

1. A composition for assaying for nitrites comprising a diazotizable amine, an acid component and a coupling component, wherein said coupling component comprises a compound of the following formula I:

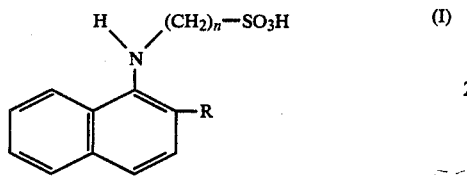

wherein R represents a hydrogen atom or a straight-chain alkyl group having 1 to 6 carbon atoms, and n represents an integer of 1 to 6, with the proviso that carbon atoms of the sulfoalkyl group may be substituted with at least 1 hydroxyl group, or a water-soluble salt thereof.

2. A composition for assaying for nitrites according to claim 1, wherein said coupling component of the formula I is a compound selected from the group consisting of:
N-(1-naphthyl)-3-aminopropanesulfonic acid,
N-(2-methyl-1-naphthyl)-3-aminopropanesulfonic acid,
N-(2-ethyl-1-naphthyl)-3-aminopropanesulfonic acid,
N-(1-naphthyl)-4-aminobutanesulfonic acid,
N-(1-naphthyl)-2-aminoethanesulfonic acid, and
N-(1-naphthyl)-3-amino-2-hydroxypropanesulfonic acid.

3. A composition for assaying for nitrites according to claim 1, wherein said coupling component of the formula I is N-(1-naphthyl)-3-aminopropanesulfonic acid.

4. A composition for assaying for nitrites according to claim 1, wherein said diazotizable amine is a compound selected from the group consisting of sulfanilamide, sulfanilic acid, arsanilic acid and p-aminobenzoic acid.

5. A composition for assaying for nitrites according to claim 1, wherein said diazotizable amine is sulfanilamide.

6. A composition for assaying for nitrites according to claim 1, wherein said acid component is a compound selected from the group consisting of tartaric, citric, oxalic, malic, malonic, succinic and glutaric acids.

7. A composition for assaying for nitrites according to claim 1, wherein said acid component is tartaric or citric acid.

8. A composition for assaying for nitrites according to claim 1, wherein said diazotizable amine, said acid component and said coupling component of the formula I or a water-soluble salt of the formula I are dissolved in water or an organic solvent such as methanol or ethanol.

9. A test device for assaying for nitrites, comprising a composition for assaying for nitrites supported on an absorptive carrier applied to a support, wherein said composition comprises a diazotizable amine, an acid component and a coupling component, said coupling component being a compound of the following formula I:

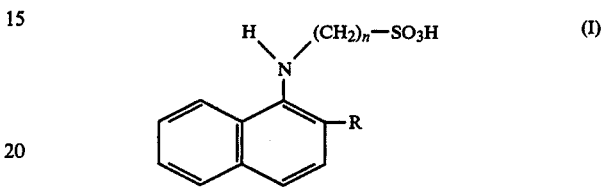

wherein R represents a hydrogen atom or a straight-chain alkyl group having 1 to 6 carbon atoms, and n represents an integer of 1 to 6 with the proviso that carbon atoms of the sulfoalkyl group may be substituted with at least 1 hydroxyl group, or a water-soluble salt thereof.

10. A test device for assaying for nitrites according to claim 9, wherein said coupling component of the formula I is N-(1-naphthyl)-3-aminopropanesulfonic acid.

11. A test device for assaying for nitrites according to claim 9, wherein said absorptive carrier is filter paper.

12. A test device for assaying for nitrites according to claim 9, wherein said support is a plastic sheet.

13. A process for assaying for nitrites, comprising contacting a substance to be assayed for nitrites with a composition comprising a diazotizable amine, an acid component and a coupling component, and observing a color change indicative of the presence of nitrites in said substance, wherein said coupling component comprises a compound of the following formula I:

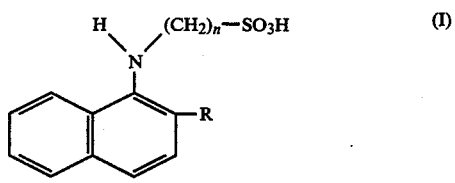

wherein R represents a hydrogen atom or a straight-chain alkyl group having 1 to 6 carbon atoms, and n represents an integer of 1 to 6, with the proviso that carbon atoms of the sulfoalkyl group may be substituted with at least 1 hydroxyl group, or a water-soluble salt thereof.

14. A process for assaying for nitrites according to claim 13, wherein said composition is supported on an absorptive carrier applied to a support.

* * * * *